(12) United States Patent
Caiafa et al.

(10) Patent No.: US 9,238,808 B2
(45) Date of Patent: Jan. 19, 2016

(54) MODULAR ADJUSTABLE PULSE GENERATOR

(71) Applicant: General Electric Company, Schenectady, NY (US)

(72) Inventors: Antonio Caiafa, Albany, NY (US); Vasile Bogdan Neculaes, Niskayuna, NY (US); Andrew Soliz Torres, Niskayuna, NY (US); Allen Lawrence Garner, West Lafayette, IN (US)

(73) Assignee: General Electric Company, Niskayuna, NY (US)

( * ) Notice: Subject to any disclaimer, the term of this patent is extended or adjusted under 35 U.S.C. 154(b) by 356 days.

(21) Appl. No.: 13/911,987

(22) Filed: Jun. 6, 2013

(65) Prior Publication Data

US 2014/0363881 A1    Dec. 11, 2014

(51) Int. Cl.
| | |
|---|---|
| *H03K 3/017* | (2006.01) |
| *C12N 13/00* | (2006.01) |
| *H02J 7/00* | (2006.01) |
| *H03K 3/57* | (2006.01) |

(52) U.S. Cl.
CPC ............... *C12N 13/00* (2013.01); *H02J 7/0052* (2013.01); *H03K 3/57* (2013.01); *Y10T 307/707* (2015.04)

(58) Field of Classification Search
CPC ........... G11C 13/0069; G11C 13/0004; G11C 13/0007; G11C 13/0028; G11C 11/36
See application file for complete search history.

(56) References Cited

U.S. PATENT DOCUMENTS

| | | | |
|---|---|---|---|
| 4,935,223 A | 6/1990 | Phillips | |
| 5,773,228 A | 6/1998 | Reed et al. | |
| 5,840,499 A | 11/1998 | Brass et al. | |
| 6,432,119 B1 | 8/2002 | Saadat | |
| 6,773,669 B1 | 8/2004 | Holaday et al. | |
| 7,029,916 B2 | 4/2006 | Dzekunov et al. | |
| 7,141,425 B2 | 11/2006 | Dzekunov et al. | |
| 7,186,559 B2 | 3/2007 | Dzekunov et al. | |
| 7,565,201 B2 | 7/2009 | Blackmore et al. | |
| 7,771,660 B2 | 8/2010 | Gabriel | |
| 7,875,296 B2 | 1/2011 | Binette et al. | |
| 8,000,813 B2 | 8/2011 | Schoenbach et al. | |
| 2001/0001064 A1 | 5/2001 | Holaday | |
| 2007/0139090 A1* | 6/2007 | Cassel | 327/181 |
| 2008/0103529 A1 | 5/2008 | Schoenbach et al. | |
| 2009/0209017 A1* | 8/2009 | Ragsdale | 435/173.6 |
| 2010/0148733 A1* | 6/2010 | Koeppl et al. | 323/225 |
| 2010/0280513 A1 | 11/2010 | Juergen et al. | |
| 2011/0318319 A1 | 12/2011 | Hargrave et al. | |
| 2012/0035511 A1 | 2/2012 | Schoenbach et al. | |
| 2012/0088842 A1 | 4/2012 | Dzekunov | |
| 2012/0109263 A1 | 5/2012 | Kolb et al. | |

OTHER PUBLICATIONS

Ok, Seung-Bok, "Design of a High-Efficiency 40-kV, 150-A, 3-kHz Solid-State Pulsed Power Modulator," IEE Transactions on Plasma Science, vol. 40, No. 10, Oct. 2012, pp. 2569-2577.

Xiao, S., "Pulsed Power for Wound Healing," 2008, pp. 69-72.

Lonza, "Amaxa Nucleofector 2b Manual for Research Use Only," 2011, pp. 1-20.

* cited by examiner

*Primary Examiner* — Sibin Chen
(74) *Attorney, Agent, or Firm* — Eileen B. Gallagher (57) ABSTRACT

A pulse generation system for applying electric pulses across a load includes a first plurality of energy storage modules connected in series on a positive chain and configured to apply a positive potential to the load and a second plurality of energy storage modules connected in series on a negative chain and configured to apply a negative potential to the load. Each energy storage module of the positive chain and the negative chain includes a rectifier and a storage element, and at least one control element.

16 Claims, 10 Drawing Sheets

MODULAR ADJUSTABLE PULSE GENERATOR

BACKGROUND

The subject matter disclosed herein relates to a pulse generator circuit, particularly a pulse generator circuit utilizing a modular approach for generating compressed pulses of adjustable duration and amplitude.

Pulsed power has numerous applications in industry such as medical treatment, biotechnology, food processing, water treatment (e.g., water purification), exhaust gas treatment, ozone generation, and ion implantation. Unfortunately, certain types of pulse generation technology are limited to generation of pulses having a set amplitude, shape, and duration. Some applications in which electric pulses are used (e.g., platelet activation, electroporation) could benefit from the ability to create a series of electric pulses that vary in amplitude, shape, and duration. Currently, for a given pulse-generation device, awkward and time-consuming hardware modifications are involved in creating pulses with a different amplitude or duration. Additional concerns in many environments in which pulse generators are used include, ease of use, the need for physical isolation, and space limitations. There is therefore a need for a system of pulse generation that is configurable in command software rather than hardware, is able to generate pulses, pulse patterns, and pulse clusters of variable duration and amplitude, and is relatively compact while maintaining appropriate physical isolation of components.

BRIEF DESCRIPTION

In one embodiment, a pulse generation system for applying electric pulses across a load includes a first plurality of energy storage modules connected in series on a positive chain and configured to apply a positive potential to the load and a second plurality of energy storage modules connected in series on a negative chain and configured to apply a negative potential to the load. Each energy storage module of the positive chain and the negative chain includes a rectifier and a storage element, and at least one control element.

In another embodiment, an electric pulse generation system includes a first plurality of energy storage modules connected in series on a positive chain configured to apply a positive potential to a load, and a second plurality of energy storage modules connected in series on a negative chain configured to apply a negative potential to the load. Each respective energy storage module of the positive chain and the negative chain includes at least one control element configured to bypass the respective energy storage module from or insert the respective energy storage module into its respective chain, and a processor configured to receive an input related to one or more characteristics of a pulse and provide instructions to the at least one control element of each respective energy storage module based on the input to insert or bypass the respective energy storage module.

In yet another embodiment, an electric pulse generation system includes a first plurality of energy storage modules connected in series on a positive chain configured to apply a positive potential to a load, a second plurality of energy storage modules connected in series on a negative chain configured to apply a negative potential to the load and a processor. The processor is configured to receive a first input related to one or more characteristics of a pulse and provide first instructions to a plurality of control elements coupled to respective energy storage modules based on the first input, and receive a second input related to one or more characteristics of a pulse and provide second instructions to the plurality of control elements based on the second input. The first instructions comprise instructions to bypass a first subset of the energy storage modules of the first plurality of energy storage modules and/or the second plurality of energy storage modules and the second instructions comprise instructions to bypass a second subset of the energy storage modules of the first plurality of energy storage modules and/or the second plurality of energy storage modules.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

As discussed in detail below, embodiments of the present technique function to provide a system for generating pulses of variable width and amplitude. Provided herein are techniques for providing electrical pulses using a modular approach allowing for user-initiated, automatic adjustment of amplitude and duration. In one embodiment, a system includes multiple energy storage modules connected in series on a chain providing positive potential, and multiple energy storage modules connected in series on a chain providing negative potential. The negative potential, positive potential, or a combination of the negative and positive potentials is applied across a load to create potential of certain amplitude. Further, control elements including high voltage fast switches and control systems allow for fast switching and generation of pulses having segments with varying durations.

In circuit design, maintaining adequate clearance distance between components may prevent dielectric breakdown between electrodes caused by the ionization of air. Because adequate clearance distances increase with the working voltage experienced by a circuit, many high powered pulse generators require significant amounts of space. In embodiments described herein, the use of a positive chain and the negative chain relaxes the clearance required between system components, resulting in a more compact system.

Further, storage elements in a pulsed power system may benefit from a specially adapted charging source for example, to provide power that is isolated from the source, and that is of a certain frequency. Accordingly, some embodiments include devices with a charging unit DC power source connected across an H bridge providing an AC current across a primary winding of a transformer, and outputs on secondary windings on the transformer for each module of the pulse generation system.

Specific applications of pulsed power may benefit from coupling systems that are tailored to a specific type of load. Accordingly, in some embodiments, the load may be a biological load placed in a cuvette with certain characteristics that reduce the chance of breakdown (e.g., arcing). In other embodiments, the coupling of the pulse generation system to a load may be by direct current, inductive coupling, or capacitive coupling. The disclosed techniques may be implemented, for example, in medical treatment, biotechnology, food processing, water treatment (e.g., water purification), exhaust gas treatment, ozone generation, and ion implantation. In particular, the samples exposed to the pulsed electric field may be samples used in medical treatment, biotechnology, food processing, water treatment (e.g., water purification), exhaust gas treatment, ozone generation, and/or ion implantation techniques.

Figure 1:
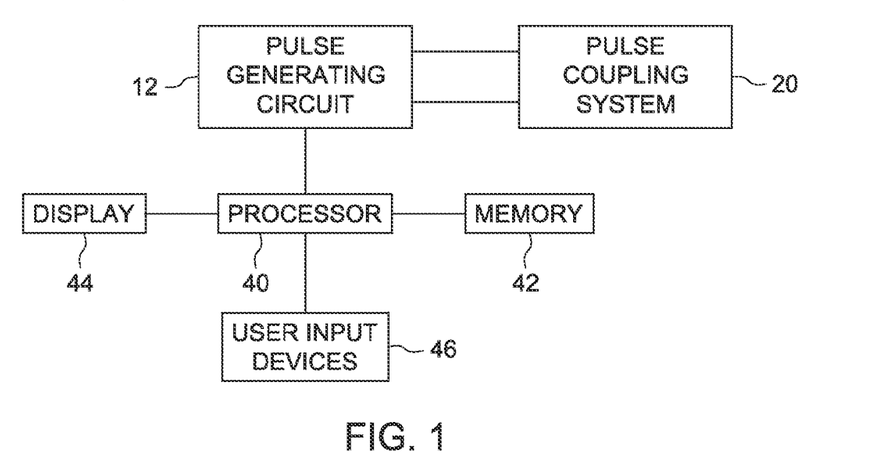
FIG. 1 is a block diagram illustrating an embodiment of a pulse generation system.

FIG. 1 shows schematically a system 10 for pulse generation. The pulse generation system 10 includes an adjustable pulse generating circuit 12 and load coupling system 20 (e.g., a cuvette including a sample for exposure to the pulsed electric field) for coupling a load to the system 10. In certain embodiments, the pulse generation system 10 may include suitable control and input circuitry and may be implemented in a dedicated housing. Alternatively, the system 10 may be coupled to a computer that provides some control and/or monitoring of the pulse generation system 10. The system 10 may include a processor 40 that controls the electric field generator 12. Additional components of the pulse generation system 10 may include a memory 42 for storing instructions that are executed by the processor 40. Such instructions may include protocols and/or parameters for the electric field generated by the electric field generator 12. The processor 40 may include, for example, general-purpose single- or multi-chip microprocessors. In addition, the processor 40 may be any conventional special purpose processor, such as an application-specific processor or circuitry. The memory 42 may be a mass storage device, a FLASH memory device, a removable memory, etc. In addition, a display 44 may provide indications to an operator related to the operation of the pulse generation system 10. The system 10 includes a user input device 46 (e.g., a keyboard, mouse, touchscreen, trackball, hand held device such as a tablet computer, PDA, smart phone or any combination thereof) for activating the electric field generator 12 and/or selecting appropriate parameters.

Figure 2:
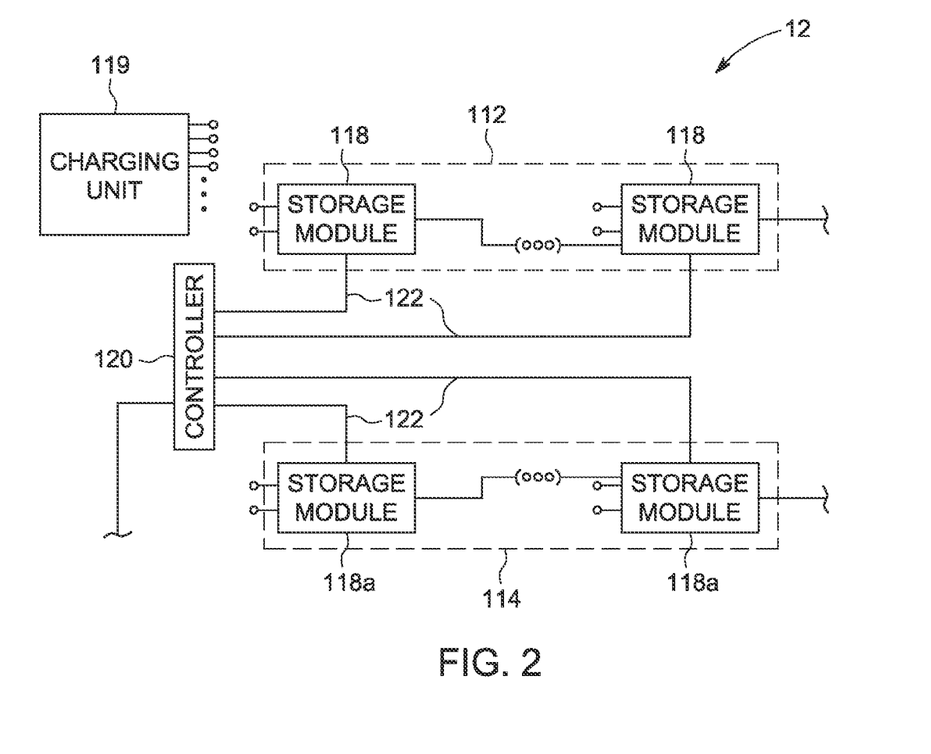
FIG. 2 is a block diagram illustrating an embodiment of a modular adjustable pulse generating circuit with a positive chain providing positive potential and a negative chain providing negative potential.

FIG. 2 is a block diagram illustrating an embodiment of the pulse generating circuit 12 of FIG. 1 that may be incorporated into any suitable pulse generation system 10. As depicted, the circuit 12 includes an upper portion, herein referred to as the positive chain 112 and a lower portion, herein referred to as the negative chain 114. However, it should be understood that the physical positions of the positive chain 112 and negative chain 114 on the circuit 12 may be exchanged and/or may be in any suitable configuration relative to ground for providing the pulsed electric field. The positive chain 112 and negative chain 114 are each electrically coupled to opposite sides of the load coupling system 20. The positive chain 112 includes of one or more storage modules 118 in series. As discussed below, the positive chain 112 is configured to apply positive potential to one side of the load. As also discussed below, the negative chain 114 is configured to provide negative potential on the opposite side of the load coupling system 20. The positive 112 and negative chains 114 each include one or more modules 118 in series. Each storage module 118 contains elements that collect charge from a charging unit 119 and store the energy until the storage module 118 is applied to contribute to a pulse.

As discussed below, each storage module 118 also includes control elements that allow it to be inserted into the line or bypassed, i.e., bypassed such that the stored energy of the bypassed storage module 118 does not contribute to the associated chain. The arrangement of the storage modules 118 in series allows for the energy stored in the individual storage modules 118 to be added together when they are inserted into the circuit. A decoder 120 receives a control signal from the processor 40 and sends control signals on individual control lines 122 coupled to each storage module 118. Control signals received from the decoder on the respective control lines 122 direct the individual storage modules 118 to either be inserted and applied to contribute to the total applied voltage or bypassed. Control logic within the individual storage modules 118 is discussed in greater detail below. Every storage module 118 that is inserted into the circuit contributes to the overall potential difference experienced by the load coupling system 20. Through this individual control of each storage module 118, the magnitudes of pulsed power applied across the load are able to be varied.

Figure 3:
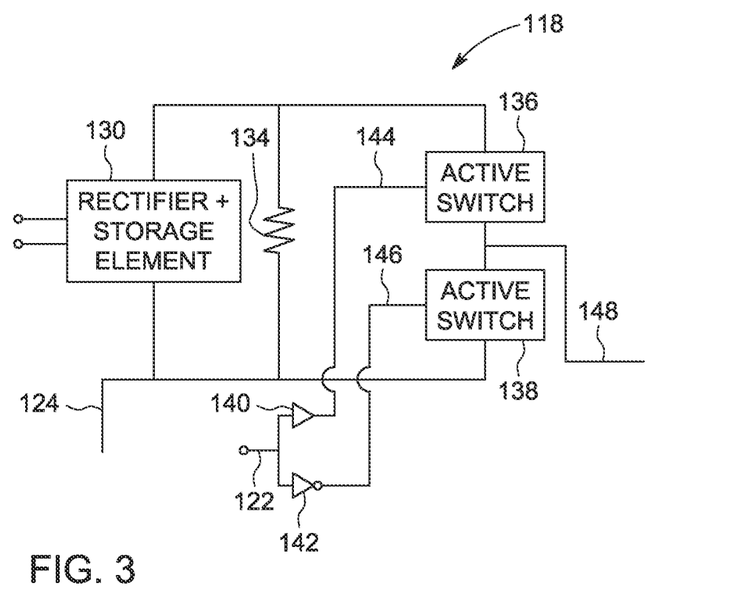
FIG. 3 is a schematic illustration of an embodiment of a storage module of the positive chain of FIG. 2.

FIG. 3 is a schematic of an embodiment of an example of a storage module 118 of the positive chain 112 of FIG. 1. When the storage module 118 is the first in the positive chain 112, the bottom leg 124 of the module will be tied to ground. The configuration relative to ground 124 permits the storage module 118 to provide a positive charge to the load coupling system 20. The storage module 118 includes a rectifier and storage element 130 that is charged via the charging unit 119, described below. The rectifier and storage element 130 may include one or more high voltage energy storage capacitors (e.g. a capacitor bank). In other embodiments, the rectifier and storage elements may include high voltage energy storing inductors, a combination of energy storing capacitors, inductors, and batteries, or any other high voltage energy storing components. A resistor 134 in series with the rectifier and storage element 130 may act as a stabilizing load. For example, the resistor 134 may absorb overflow charge when the rectifier and storage element 130 has reached capacity due to for example an unbalanced power supply. Also tied across the rectifier and storage element are a first switch 136 on a high side of a half bridge circuit and a second switch 138 on a low side of the half bridge. As discussed below, each switch 136 and 138 may be an active switch that allows for generation of pulses with a relatively steep rise, known as pulse compression.

As shown, the control line 122 is connected to inputs of a buffer 140 and an inverted buffer 142. The output 144 of the buffer 140 is connected to the gate of the first switch 136. The output of the inverted buffer is connected to the gate of the second switch 138. Because the buffers 140 and 142 share an input with the control line 122 of the storage module 118, a single signal on the control line 122 can control the pair of switches 136 and 138 substantially simultaneously, and oppositely. For example, the processor 40 of FIG. 1 may send a signal to the decoder 120 that is translated into a signal in a high state. This high state signal is transmitted along the control line 122 to its respective storage module 118. The buffer 140 outputs a signal 144 that mirrors the input, in this case, a high state signal. The output of the buffer (e.g., the high state signal) is received by the first switch 136, activating it. At the same time, the inverted buffer 142 provides an output 146 opposite to the input. Therefore a high signal on the control line 122 results in a low signal on the output 146 of the inverted buffer 142. The low signal received by the second switch 138 leaves it in a deactivated (e.g., open) state. Thus, the single control signal is able to simultaneously control the first switch 136 and second switch 136 oppositely.

The activation of the first switch on the high side of the half bridge inserts the rectifier and storage element 130 of the storage module 118 into the positive chain 112. The module output 148 of each storage module 118 is tied to the bottom leg 124 of each subsequent module 118. This configuration places each inserted rectifier and storage element 130 in series allowing the applied power to be added.

Figure 4:
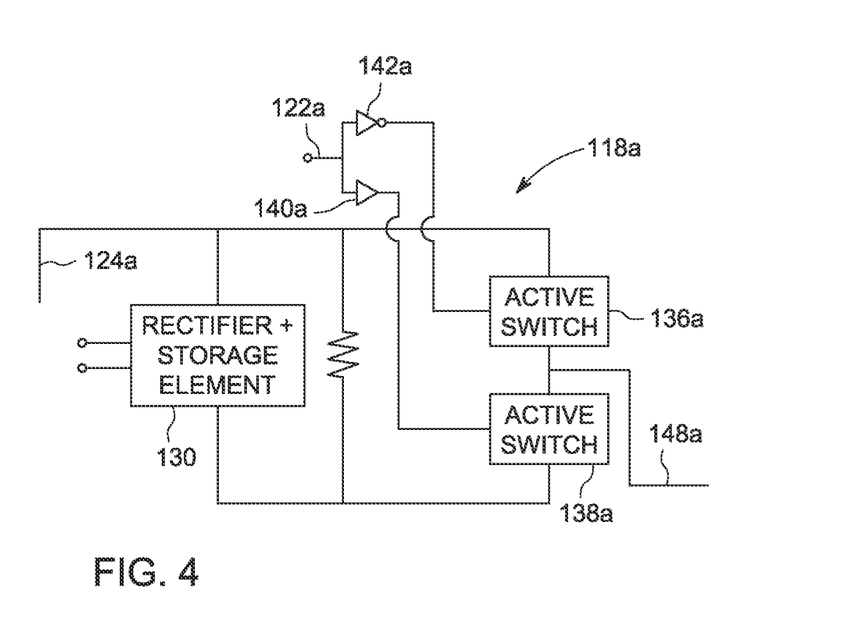
FIG. 4 is a schematic of an embodiment of one of the storage modules of the negative chain of FIG. 2.

FIG. 4 is a schematic of an embodiment of one of the storage modules 118a of the negative chain 114 of FIG. 2. The first storage module on the negative chain the high side 124a of module half bridge is tied to ground. The grounding of the high side reverses the polarity of the voltage drop across the rectifier and storage elements 130, resulting in the negative voltage drop desired in the negative chain 114. As with the storage modules 118 on the positive chain 112, the output 148a of each storage module 118a on the negative chain 114 is tied to the high side 124a of each subsequent module 118a, allowing each rectifier and storage element 130 to be tied in series upon being inserted by the control elements. This configuration allows the series of elements on the negative chain 114 to produce a voltage with absolute value proportional to the number of modules inserted, but negative with respect to ground.

As illustrated, control line 122a for the storage module 118a on the negative chain 114 is connected to inputs of a buffer 140a and an inverted buffer 142a. The output 144a of the buffer 140a is connected to the gate of the first switch 136a. The output of the inverted buffer 142a is connected to the gate of the second switch 138a. Similarly to the control line 122 on the storage module 118 on the positive chain 122, the buffers 140a and 142a shown share an input with the control line 122a of the storage module 118a. Thus, a single signal on the control line 122a can control the pair of switches 136a and 138a substantially simultaneously, and oppositely. But, because of the reverse configuration of the buffers (i.e., the output of the buffer 140a is tied to the second switch 138a and the output of the inverted buffer 142a is tied to the first switch 136a) the behavior of the storage module 118a is reversed. For example, a high state signal transmitted along the control line 122a to its respective storage module 118a will result in a high signal output from the buffer 140a and a low signal output from the inverted buffer 142a. The output of the buffer (e.g., the high state signal) is received by the second switch 138a, placing it in an activated (e.g. closed) state. At the same time, the first switch 138a receives the low signal output of the inverted buffer 142a, leaving the switch 138a in a deactivated (e.g., open) state. Thus, the single control signal is able to simultaneously control the first switch 136 and second switch 136 oppositely.

The activation of the second switch 138a on the low side of the half bridge bypasses the rectifier and storage element 130 of the storage module 118a so that its charge is not added to the charge applied by the negative chain 114. Thus, a high signal applied to the control line 122a of the module 118a results in a bypassed module, while a high signal applied to the control signal 122, as pictured in FIG. 3, results in an inserted module 118. As with the positive chain 112, the module output 148a of each storage module 118a on the negative chain 114 is tied to the bottom leg 124 of each subsequent module 118. This configuration places each inserted rectifier and storage element 130 in series, allowing the applied power to be added or bypassed.

Figure 5:
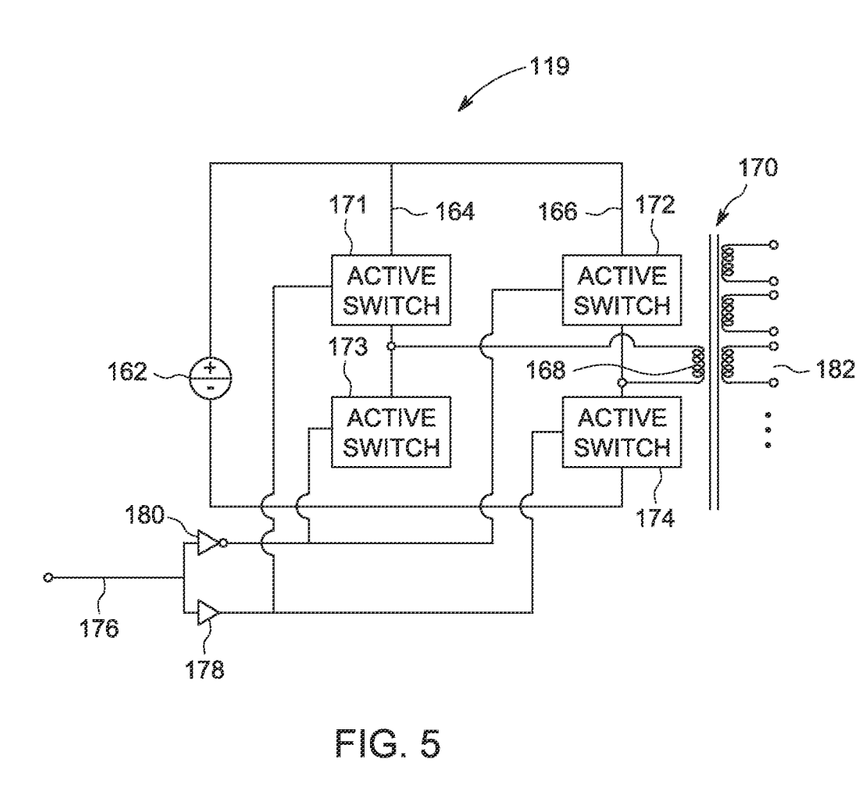
FIG. 5 is a schematic of an embodiment of the power source of FIG. 1.

FIG. 5 is a schematic of an embodiment of the charging unit 119 of FIG. 2. As shown, a DC power supply 162 is connected across an H bridge. The H bridge consists of two circuit branches 164 and 166 connected across the DC power source 162. The two branches 164 and 166 are bridged by outputs to the primary winding 168 of a transformer 170. Each branch 164 and 166 of the H bridge contains a high switch 171 and 172 located on the branch on one side of the output and a low switch 173 and 174 located on the branch below the output. A control line 176 is connected to a buffer 178 and inverted buffer 180. The control signal sent on the control line 176 may be tied to the same processor 40 and decoder 120 that controls the insertion or bypass of the modules. In other embodiments, the control signal for the charging unit 119 may be tied to a separate processor or a dedicated controller. The buffer 178 outputs to the high switch 171 on one branch and the low switch 174 on the other. The inverted buffer 180 outputs to the other two switches 172 and 173. In this manner, a control signal 176 can simultaneously and oppositely operate each set of switches. Thus AC power of a desired frequency is provided to the first winding 168 of the transformer. The transformer includes one secondary winding 182 for each storage module 118 to be powered. The output of each secondary winding 182 is routed to the input of the rectifier and power storage elements 130 of each storage module 118, as shown in FIG. 2. In some embodiments, feed-forward control may be used to control the H bridge of the charging unit 119. That is, because the processor receives user input corresponding to the desired pulses or pulse patterns before the power is supplied, the processor may control the H bridge to charge to individual storage modules in advance of application. In this way, the charging of the storage modules is not controlled reactively by the load, but instead by the external control of the processor directing the operation of the H bridge. In this way the storage modules 118 and 118a may remain charged at higher levels for longer periods, retaining more even power levels with less fluctuation after applying power to the load. Control of the charging unit may also enable storage modules to apply voltages lesser than their capacity. For example, storage modules with a capacity of 1 kV may be charged with a voltage of only 800V (e.g., by controlling H bridge frequency or the input DC voltage). This may enable the pulse generation system greater flexibility, specifically, the ability to apply pulses with amplitudes that are a multiples of different voltages (e.g., multiples of 800V instead of multiples of 1 kV).

Figure 6:
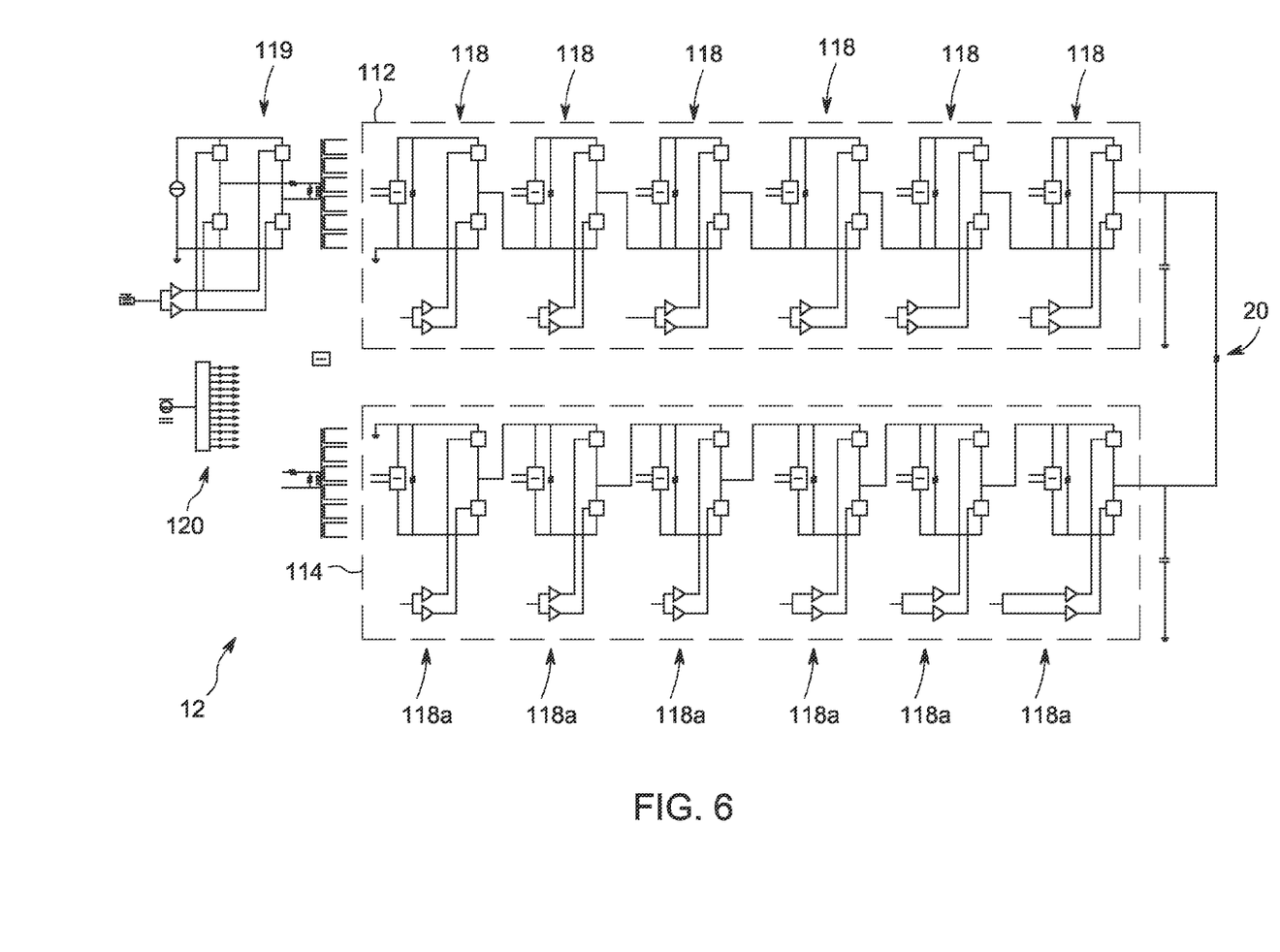
FIG. 6 is a schematic illustration of an embodiment of the modular pulse generator of FIG. 2 not explicitly including local pulse compression.

FIG. 6 illustrates an embodiment of the pulse generation system 10 including six modules 118 on the positive chain 112 and six modules 118 on the negative chain 114 not explicitly including local pulse compression. As discussed in greater detail below, the implementation of certain active switch technology may enable pulse compression on a local or modular level. Each module 118 in the illustrated embodiment may be configured to provide approximately 1 kilovolt (kV); however, it should be understood that the storage modules 118 may be configured to store more or less potential. Each storage module 118 inserted (e.g., not bypassed and applied) on the positive chain 112 creates a positive potential that is combined with any negative potential created by the storage modules 118 inserted on the negative chain 114. That is, if all six modules 118 on the positive chain 112 are inserted to create 6 kV of positive potential. Similarly, if all six modules 118 on the negative chain 114 are inserted, −6 kV of potential is generated on the negative chain 114. Thus, by tying one side of the load coupling system 20 each to the positive chain 112 and negative chain 114, a combined potential of approximately 12 kV is able to be applied across the load coupling system 20. It should be understood that because each module may be individually controlled, operation of the chains may be asymmetrical. For example, one module 118 of the positive chain may be inserted, and 3 modules 118a of the negative chain may be inserted to apply a potential of approximately 4 kV. Further, an embodiment with 6 modules on each of the positive and negative chains can provide pulses with amplitude of 1, 2, 3, 4, 5, 6, 7, 8, 9, 10, 11, or 12 kV. For example, if 8 kV is desired, multiple combinations of modules 118 on the positive and negative chains 112 and 114 may be inserted to create 8 kV (e.g. any four positive modules combined with any four negative modules, all six positive modules combined with any two negative modules, any two positive modules combined with all six negative modules, any five positive modules combine with any three negative modules, any three positive modules combined with any five negative modules, etc.). Accordingly, the system 10 has multiple possible pathways for creating the desired pulse amplitude by activating the positive chain 112 and the negative chain 114 at the same time (e.g., simultaneously). In this manner, a pulse generation system 10 may be created with any suitable number of energy storage modules 118 in the positive chain 112 and the negative chain 114 based on the desired electric field strength and/or range of strengths of the generated pulses. Thus, adding more energy storage modules to the positive chain 112 and/or the negative chain 114 may increase the possible range of amplitudes. In certain embodiments, the number of energy storage modules 118 on the positive chain 112 and the negative chain 114 are equal.

The dual-chain configuration of present embodiments, in which each of the two chains is capable of contributing a portion of (e.g., roughly half) the potential across the load, yields a more compact circuit design. This is due to the relaxed clearance design requirements for components in the dual-chain circuit design. That is, usage of components with significantly more lenient clearance requirements (e.g., requirements for physical separation of circuit elements and dielectric materials) may be used when compared to a similar circuit using only one chain. For example, in the embodiment illustrated in FIG. 6, 12 kV of potential is able to be generated by the circuit. But, due to the dual-chain configuration, the components only experience up to 6 kV of working voltage. Because elements are rated for 6 kV, the required clearances are lesser than if elements were to be rated for a working voltage of 12 kV. Further, because required clearances increase greater than linearly in relation to potential rating of circuit components, significant space savings are possible. For example, in the present embodiment, the clearance requirements are less than half for the elements rated for 6 kV as compared to elements that would be rated at 12 kV. Thus, using the two chain configuration, the circuit is able to have much smaller size than a single-chain circuit design providing the same potential.

Figure 7:
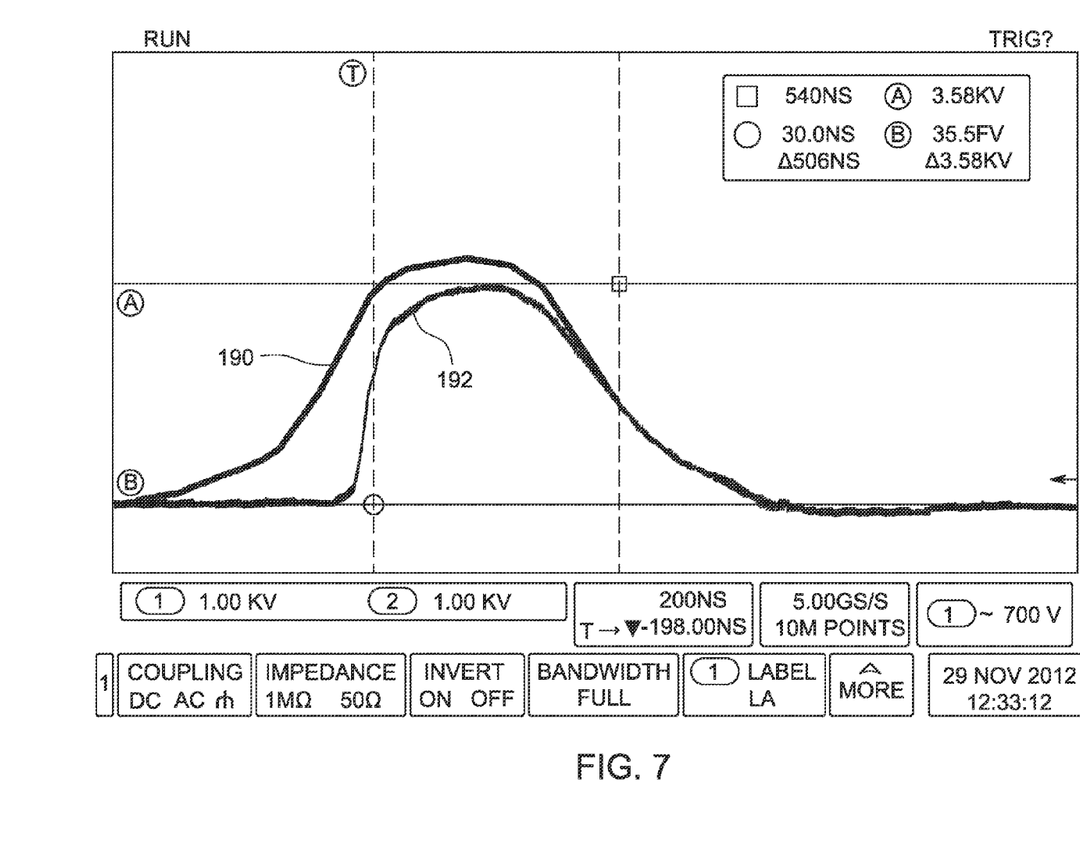
FIG. 7 is a graph illustrating an uncompressed pulse and a compressed pulse generated by an embodiment of the present disclosure.

FIG. 7 is a graph illustrating an uncompressed pulse 190 and a compressed pulse 192 generated by certain embodiments of the present disclosure. In many applications of pulsed power, it is desirable to have a pulse with a steep rise, as seen in the compressed pulse 192. Described below are embodiments that implement fast active switches to enable the desired steep rise.

Figure 8:
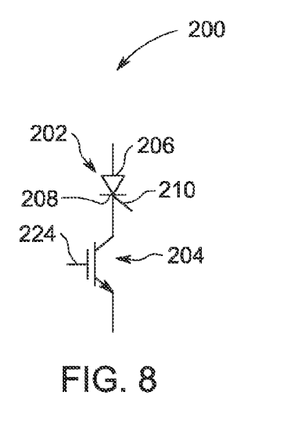
FIG. 8 is an illustration of an embodiment of a fast active switch including a thyristor acting in breakover mode, that may be used as the first and second switch of a module as shown in FIGS. 3 and 4 to enable local pulse compression and switching.

FIG. 8 is an illustration of an embodiment of a fast active switch 200 that may be used as the first 136 and second switch 138 of a module as shown in FIGS. 3 and 4. The implementation of this fast active switch enables pulse compression on the local (e.g., modular) level. In this embodiment, the active switch 200 includes a thyristor 202 and an IGBT 204. In other embodiments the thyristor 202 may be combined with other active switch technologies (e.g, MOSFET, MCT, thyristor, BJT). The switch 204 may also be composed of various materials (e.g., Si, SiC, GaN). The thyristor 202 acting in its normal mode of operation is an efficient electronic switch able to provide control at very high power levels with very low power dissipation. As shown in FIG. 8, the thyristor 202 includes an anode 206, cathode 208, and gate 210.

Figure 8A:
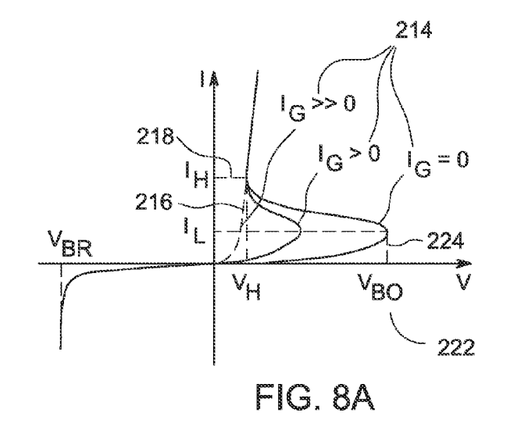
FIG. 8A is a graph of the voltage-current characteristics of the thyristor of FIG. 8 that allow the thyristor to enable fast switching and local pulse compression.

FIG. 8A is a graph of the voltage-current characteristics 212 of a thyristor 202. When used independently as a switch, gate to cathode current $I_G$ 214 locks the thyristor 202 into an "on" state 216. The thyristor 202 remains in the "on" state even if the triggering voltage is removed, and remains "on" until the anode to cathode current drops below the holding current $I_H$ 218. In certain embodiments, the switching action of the thyristor 202 is too slow to create pulses of the desired compression (e.g., pulses with fast rise times as illustrated in FIG. 7). Therefore, an IGBT 204 may be included in series with the thyristor 202. The IGBT 204 supports a voltage greater than the breakdown voltage $V_{BO}$ 222 of the thyristor. When a high control signal (e.g. a signal from an output of the buffer or inverted buffer of FIG. 2) is received at the gate 224 of the IGBT 204, the IGBT 204 is activated. The activated IGBT 204 acts as a closed switch so that the voltage exceeding $V_{BO}$ 222 that had been supported by the IGBT 204 is then supported by the thyristor 202. As seen in FIG. 6, at $V_{BO}$ 222 the thyristor 202 undergoes a fast switch independent from any gate current $I_G$ 214. This behavior is known as the breakover condition of the thyristor 202 and allows it to act as a fast switch. Due to the characteristics of the thyristor 202 allowing it to support high voltages, the combination of the thyristor 202 and IGBT 204 create the fast active switch 200 able to support high voltages. Because each storage module 118 may be individually controlled using this fast active switch 200, pulse compression is achieved on a distributed basis (i.e., within each individual module). This distributed pulse compression enables the variable pulses that may be created by the system to all be sufficiently compressed. That is, even if a pulse is the result of superimposed signals for different modules 118, because the compression is distributed throughout each module, the rise times in all segments of the pulse will remain compressed.

Figure 9:
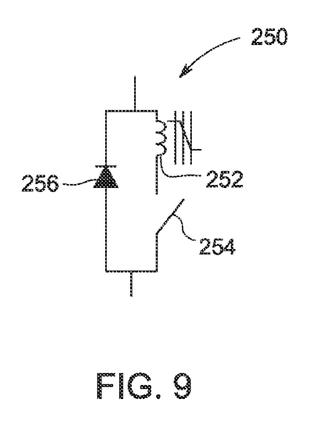
FIG. 9 is an illustration of an embodiment of a fast active switch, including a highly nonlinear magnetic core, that may be used as the first and second switch of a module, as shown in FIGS. 3 and 4.

FIG. 9 illustrates an additional embodiment of a fast active switch 250 that may be used as the first 136 and second switch 138 of a module as shown in FIGS. 3 and 4. The fast active switch 250 includes a highly nonlinear inductor (e.g., a highly non-linear magnetic core 252) and an active switch 254 in series, both in parallel to a diode 256. The switch 250 may be an IGBT, MOSFET, MCT, thyristor, BJT, or any other active switch device. The nonlinear properties of the magnetic core 252, not the speed of the switch 250, that allow the combination to operate as a fast active switch and achieve magnetic pulse compression.

Figure 9A:
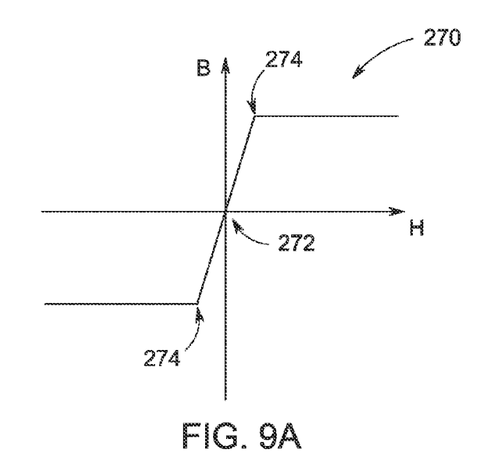
FIG. 9A is a graph illustrating the characteristic flux density to magnetic field strength behavior of a highly nonlinear magnetic core, showing the qualities that allow the nonlinear magnetic core to enable fast switching.

FIG. 9A is a graph of the characteristic flux density to magnetic field strength behavior 270 (i.e., the B-H curve) of the highly nonlinear magnetic core 252, showing the qualities that allow the nonlinear magnetic core to enable fast switching. When the switch 254 is closed, the capacitance of any load causes it to act as a short circuit, and the voltage from the storage module 118 is applied across the magnetic core 252. With current through the magnetic core 252 being zero, the magnetic field strength is also zero 272 and impedance, being proportional to the slope of the B-H curve, is very high. Therefore, the magnetic core 252 acts as an open circuit, and the input voltage is applied directly to the magnetic core 252. With time, the flux density in the nonlinear magnetic core 252 grows. When the flux density reaches $B_{sat}$ 274, the impedance of the inductor 252 rapidly becomes virtually zero creating a nearly instantaneous short circuit. It should be noted that the slope of B-H curve of the particular magnetic core device 252, not the speed of the switch 254, that influences the switching speed of the voltage applied to the load.

It is envisioned that the pulse generation system 10 as provided herein may be implemented as a single-purpose device (e.g., for platelet activation) or as a multi-purpose device that may be used for additional electric field exposure applications (e.g., electroporation, purification). Further, the system 10 may be configured to generate a pulsed electric field according to one or more protocols. The protocols may be generated by user inputs and/or may be stored in the memory 42 to be selected by the user. In one embodiment, the system 10 may operate without any user input to the activation protocol other than an input to start activation once a load is coupled to the load coupling system 20. In such an embodiment, the electric field generator 12 may operate under control of the processor 40 to operate a single protocol with predetermined electric field strength, pulse length, and/or total exposure time. Such a protocol may be determined by empirical studies. In other embodiments, the system 10 may be configured to receive a user input related to the electric field strength, pulse length, waveform shape, pulse pattern, cluster number, period of time between pulses and between clusters and/or total exposure time. In one embodiment, the system 10 may be configured to determine a most efficient path for generating the desired pulse based on the configuration of the energy storage modules 118. That is, where multiple paths are possible, the system 10 may default to the most efficient path. Further, the system 10 may be configured to generate a particular pulse shape or to generate a series of pulses that may differ from one another according to a user input and/or a stored protocol setting. Examples of various segmented and variable-amplitude signals that are able to be generated in compressed form by present embodiments are illustrated and discussed below.

In some embodiments, the load may include any kind or any number of cells in a buffer or biological fluid. The pulse generator may be coupled to the load in a variety of ways, including directly, through capacitive coupling, or through inductive coupling. Direct coupling may be achieved by the use of metallic contacts directly on the liquid. Capacitive coupling uses displacement current induced by electric plates in proximity, but isolated from the sample. Inductive coupling utilizes inductive coils in close proximity to the sample.

Figure 10:
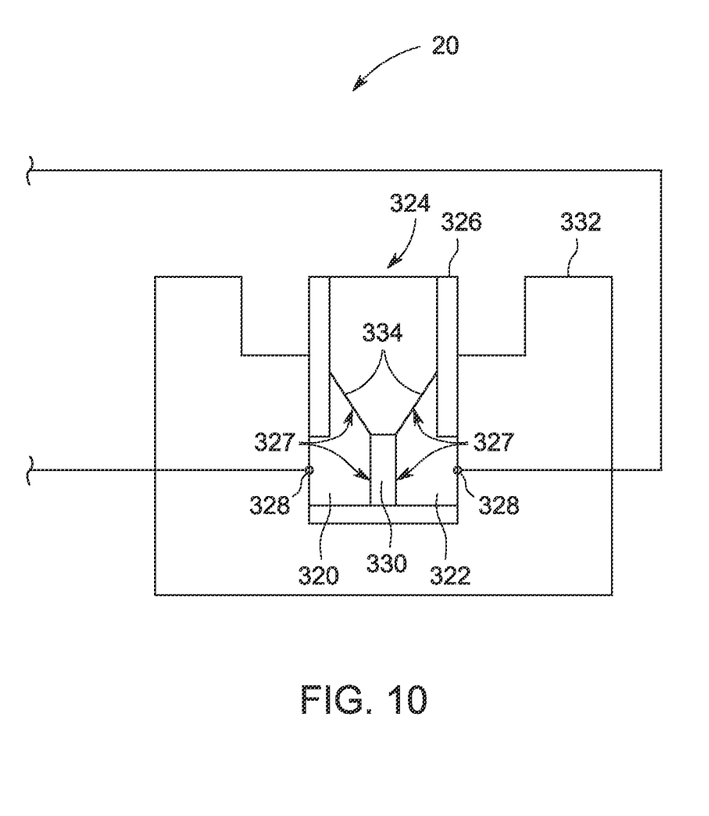
FIG. 10 is an embodiment of the load coupling system of FIG. 1.

Depicted in FIG. 10 is an embodiment of a load coupling system 20 as introduced in FIG. 1. In certain embodiments, the load coupling system 20 may include electrode sets (or arrays of electrodes) 320 and 322. In the depicted embodiment, a cuvette 324 includes a containment portion 326, and electrodes 320 and 322. The electrodes 320 and 322 are spaced apart on opposing walls of the containment 326. The containment portion 326 may be formed from a dielectric material (e.g. acrylic) that isolates the opposing electrodes 320 and 322 as well as holds the liquid sample 330 (e.g. a biological fluid containing platelets, a purification sample) in a suitable volumetric configuration. In certain embodiments, the cuvette 324 is disposable and is removable from a sample holder 332. In these embodiments, the containment portion 326 orients contacts 328 of the electrodes so that they properly align within the sample holder 332. Proper alignment puts the electrodes 320 and 322 in contact with the outputs of the pulse generation circuit 12 thereby exposing the sample 330 within the cuvette 324 to the desired electric field. As mentioned above, the containment portion 326 holds the electrodes 320 and 322 spaced apart from one another. The gap between these electrodes 320 and 322 will influence the strength of the electric field for a given applied voltage. In one embodiment, the cuvette 324 is configured to have a 1 cm gap between the electrodes 320 and 322. The electric field strength is the ratio of the applied voltage to the distance between the two electrodes and may be expressed in V/cm or kV/cm. For example, for applying 1 V across a 1 cm cuvette gives an electric field strength of 1 kV/cm. For implementations in which a smaller cuvette is used, e.g., a 0.5 cm cuvette, 500 V may be used to achieve a 1 kV/cm field strength. The location where an electrode 320 or 322, the containment portion 326, and the liquid sample 330 meet may be referred to as a triple point 327. In some embodiments, to reduce the likelihood of electrical breakdown (e.g. arcing) at the exposed area 334 of the triple point 327 (i.e., the surface of the electrode not submerged in fluid), the electrodes 320 and 322 may be tapered along the containment portion 326 wall. This tapering increases the gap between the triple points 327 and may significantly decrease the field strength along the exposed triple point 334 (e.g. reduce field strength by as much as five times).

Figure 11:
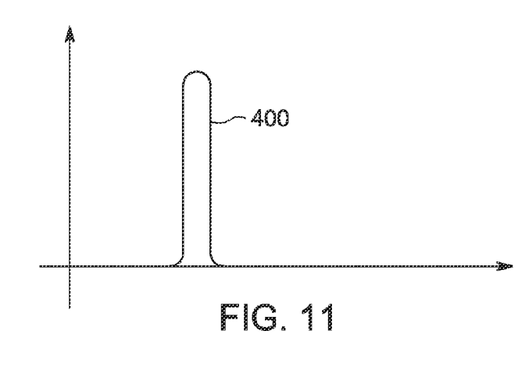
FIGS. 11-22 are examples of pulse waveforms that may be generated by embodiments of the present disclosure.
Figure 12:
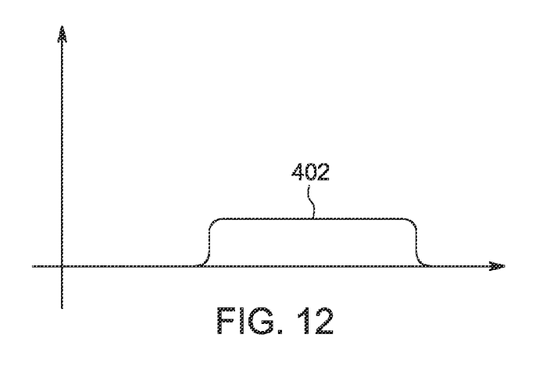
Figure 13:
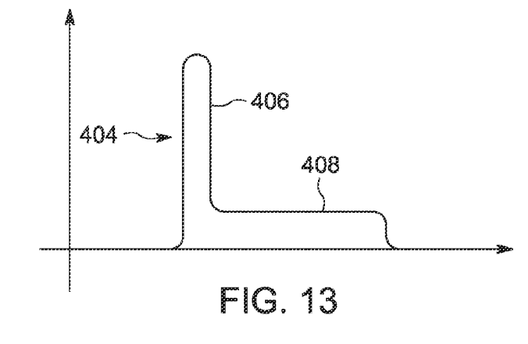
Figure 14:
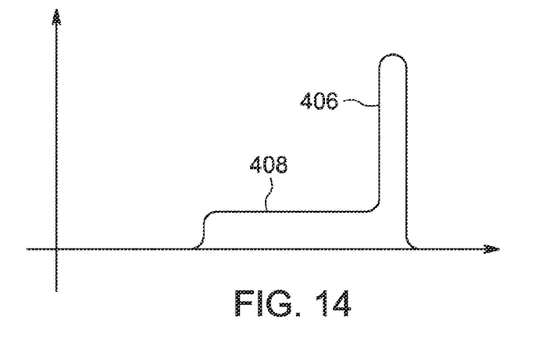

As discussed herein, the pulse generation system 10 may be configured to provide electric pulses having desired characteristics. FIGS. 11-22 show examples of pulses and/or pulse patterns that may be generated by the pulse generator system 10 and applied to a load. The pulses applied by the pulse generation system 10 may have different combinations of amplitude and duration depending on the implementation. FIG. 11 is a square wave pulse 400 with a relatively higher amplitude and shorter pulse length than the pulse 402 shown in FIG. 12. As discussed above, different amplitudes and pulse durations may be controlled by the processor 40 of the pulse generation system 10. FIG. 13 is an embodiment where a pulse 404 has a higher amplitude, shorter duration portion 406 and a lower amplitude, longer duration portion 408. The pulse 404 has a variable shape and is not a square wave. In certain embodiments, the higher amplitude, shorter duration portion 406 may target some components of a sample, and the longer duration portion 408 may affect other components of a sample. For embodiments in which a pulse of 1 microsecond or more is generated, the higher amplitude, shorter duration portion 406 is 1 microsecond to about 30 microseconds and the lower amplitude, longer duration portion 408 is 99 microsecond to about 70 microseconds. Further, the higher amplitude, shorter duration portion 406 may have an amplitude that is at least twice the amplitude of the lower amplitude, longer duration portion 408. FIG. 14 is an embodiment in which the lower amplitude, longer duration portion 408 is the first part of the pulse 410 and the higher amplitude, shorter duration portion 406 is the second part of the pulse 410. The pulses of FIGS. 13 and 14, each including at least 2 portions having varying amplitude which may or may not have different durations, may be referred to as pulse patterns. It is contemplated that in some applications it may be desirable to repeat these pulse patterns with short periods of separation to create a repeating pulse pattern (e.g., repetition of a pulse 404 three times with a 1 microsecond separation). This pulse pattern repetition may be referred to as a pulse cluster.

Figure 15:
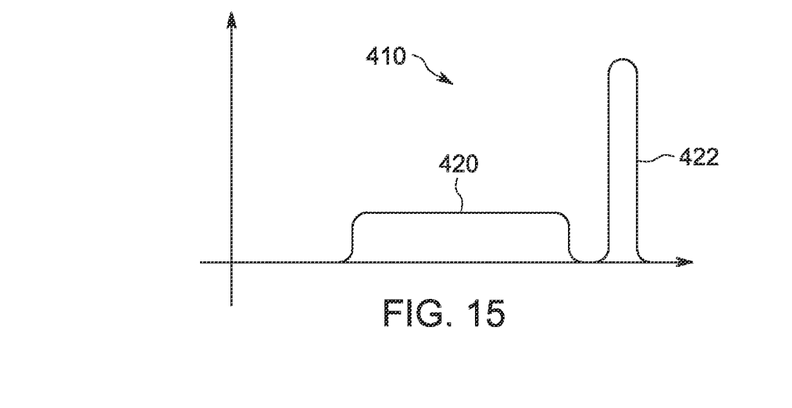
Figure 16:
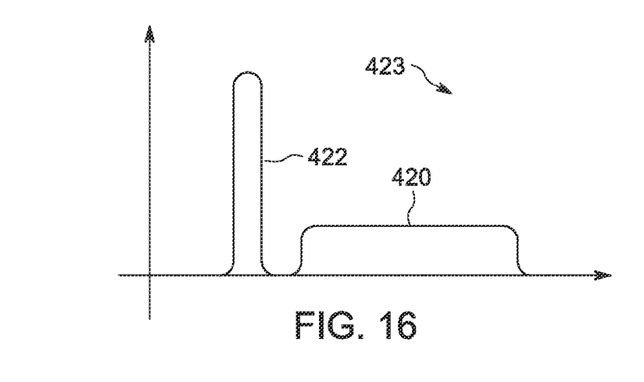
Figure 17:
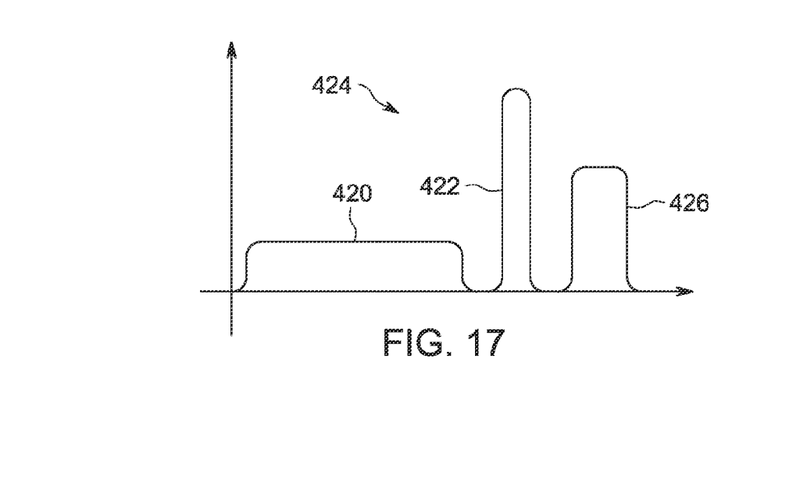
Figure 18:
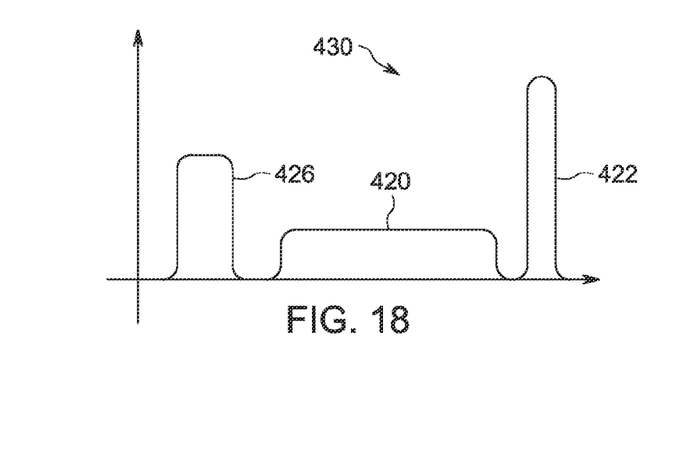

FIGS. 15-18 show different pattern combinations of square wave pulses. For example, FIG. 15 is an example of a pulse pattern 410 with a lower amplitude, longer duration pulse 420 followed by a higher amplitude, shorter duration pulse 422. FIG. 16 shows a pattern 423 in which the arrangement between the pulses 420 and 422 is reversed. For a repeating pulse pattern, the effects of the patterns 410 and 420 may be similar. FIG. 17 shows a pattern 424 in which a pulse 426 of amplitude and duration between those of the pulses 420 and 422 is part of the pattern. FIG. 18 shows an example of a different pattern 430 in which the medium amplitude and duration pulse 426 is arranged as the first pulse in the pattern 430. As with the pulse patterns illustrated in FIGS. 13 and 14, the pulse patterns in FIGS. 15-18 may be repeated to form a repeating pulse pattern that may be referred to as a pulse cluster.

Figure 19:
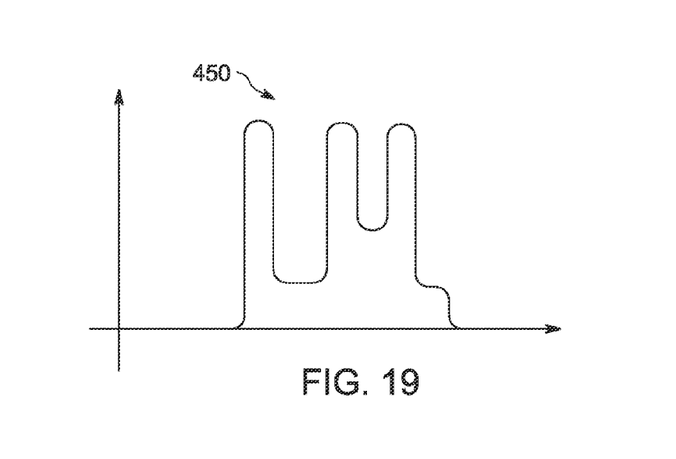
Figures 20, 22:
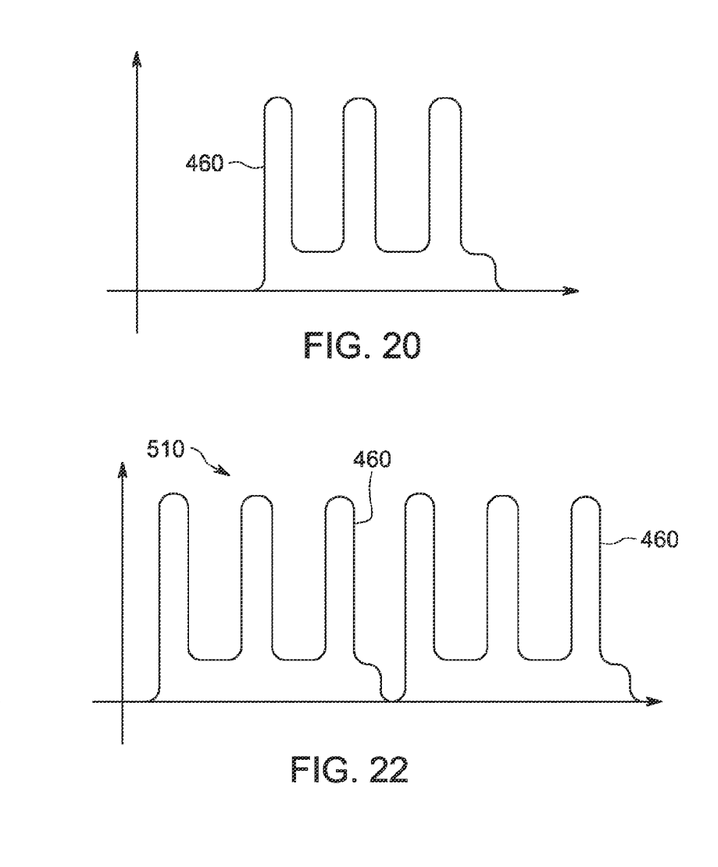
Figure 21:
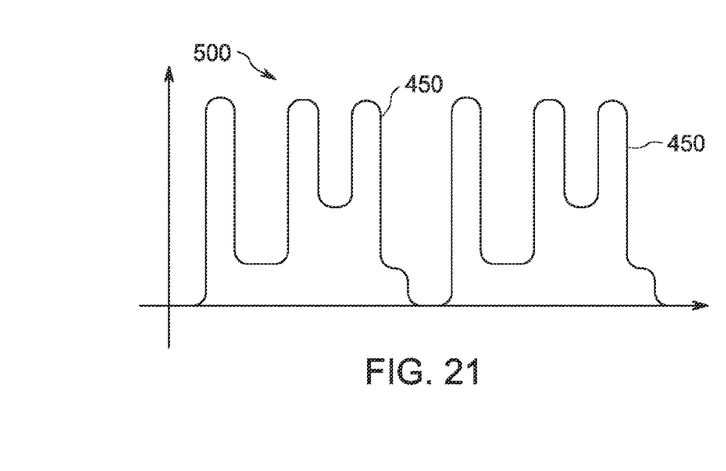

In some embodiments the number of different amplitudes able to be applied is equal to the total number of storage modules 118 and 118a included in the pulse generating circuit 12. For example, in a pulse generating circuit 12 containing 10 positive modules 118 and 10 negative modules 10, pulses of 20 different amplitudes may be generated. It is also contemplated that the pulses may include shaped patterns within each pulse. This may be enabled by the processor 40 sending control signals that insert and bypass modules 118 at various intervals during the duration of a pulse, creating pulses with amplitudes that may step up and down within the pulse. For example, FIG. 19 shows an example of a pulse pattern 450 with higher amplitude portions, lower amplitude portions, and medium amplitude portions. FIG. 20 shows an example of a pulse pattern 460 with alternating high and low amplitude portions. FIG. 21 is a pulse cluster 500 formed from a series of pulse patterns 450, and FIG. 22 is a pulse cluster 510 formed from a series of pulse patterns 460. Further, it is contemplated that pulse clusters may include combinations of different types of shaped pulses, such as pulses 450 and 460. Further, pulse clusters may be repeated to form repeated clusters. Pulse pattern repetition and pulse cluster repetition may allow for definitions of series of pulses that are more complex than individual pulses or pulse patterns. In certain embodiments, the use of multiple storage modules may allow for an energy balancing technique. That is, for patterns requiring repeated pulses or pulse patterns within a short time-span, storage modules may be alternated, utilizing a relatively "fresh" storage module for each pulse component. For example, in order to apply a pulse pattern requiring 6 repeating pulses 400 as shown in FIG. 11, using, for example, the pulse generating circuit of FIG. 6 having six storage modules 118 on the positive chain 112 and six modules 118a on the negative chain 114, the processor 14 of the pulse generating system may direct a first module 118, then a second module 118, then a third module 118 from the positive chain 112 to be applied, and then a first module 118a, then a second module 118a, and then a third storage module 118a from the negative chain 114 to be applied in series. If another similar pulse pattern is desired, the processor may direct the remaining "fresh" storage modules to be applied (i.e., the fourth, fifth and sixth storage modules 118 from the positive chain 112, and the fourth, fifth, and sixth modules 118a from the negative chain 114). This energy balancing method may provide even wear on the components, as well as additional time for individual storage modules to recharge before being re-inserted and applied to the load. Because pulses or pulse patterns may be repeated using fresh modules this technique may enable shorter delays between pulses or pulse patterns.

Technical effects of the invention include a pulse generation system with a more compact circuit design that also provides increased range and complexity in a generated pulsed electric field for a variety of applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A pulse generation system for applying electric pulses across a load, comprising:
   a first plurality of energy storage modules connected in series on a positive chain and configured to apply a positive potential to the load; and
   a second plurality of energy storage modules connected in series on a negative chain and configured to apply a negative potential to the load, wherein each energy storage module of the positive chain and the negative chain comprises:
   a rectifier and a storage element; and
   at least one control element;
      where said control element comprises a first switch and a second switch in a half bridge configuration configured to allow each energy storage module to be inserted into or bypassed by its respective chain; and
      each switch comprises an active switch and a thyristor acting in breakover mode in series or an active switch and an inductor with a highly non-linear magnetic core in series, wherein the active switch comprises an IGBT, MOSFET, MCT, Thyristor, or BJT; and
   wherein the pulses are compressed locally, on a modular level.

2. The system of claim 1, wherein the positive chain and the negative chain contribute about the same potential to the load.

3. The system of claim 1, wherein the positive chain and the negative chain contribute unequal potential to the load relative to one another.

4. The system of claim 1, wherein coupling of the pulse generation system to the load is by direct current, inductive coupling, or capacitive coupling.

5. The system of claim 1, wherein the positive chain and the negative chain have the same number of energy storage modules.

6. The system of claim 1, wherein the system comprises:
   a cuvette coupling the positive chain and the negative chain to a biological sample, wherein the cuvette comprises:

opposing electrodes disposed on opposite sides of a dielectric containment element supporting a gap between the electrodes, the electrodes having a tapered portion that tapers towards a top surface of the cuvette such that a narrowest point of the electrodes relative to one another is closer to the top surface than a widest point of the electrodes relative to one another.

7. The system of claim 1, comprising a charging unit configured to change each energy storage module.

8. An electric pulse generation system comprising:
a first plurality of energy storage modules connected in series on a positive chain configured to apply a positive potential to a load;
a second plurality of energy storage modules connected in series on a negative chain configured to apply a negative potential to the load;
wherein each respective energy storage module of the positive chain and the negative chain comprises at least one control element configured to bypass the respective energy storage module from or insert the respective energy storage module into its respective chain;
a processor configured to receive an input related to one or more characteristics of a pulse and provide instructions to the at least one control element of each respective energy storage module based on the input to insert or bypass the respective energy storage module; and
a charging unit configured to charge one or more of the first plurality of storage modules and the second plurality of storage modules, wherein the charging unit comprises an DC power source connected across an H bridge providing an AC current across a primary winding of a transformer, and outputs from a secondary winding on the transformer for each respective energy storage module, and wherein the processor is configured to operate the charging unit in a feed-forward control mode.

9. The system of claim 8, wherein the control elements comprise a first switch and a second switch in a half bridge configuration.

10. The system of claim 8, comprising:
a cuvette coupling the positive chain and the negative chain to the load, wherein the cuvette comprises:
electrodes disposed on opposite sides of a dielectric containment element, the electrodes comprising a tapered upper portion.

11. An electric pulse generation system comprising:
a first plurality of energy storage modules connected in series on a positive chain configured to apply a positive potential to a load;
a second plurality of energy storage modules connected in series on a negative chain configured to apply a negative potential to the load; and
a processor configured to:
receive a first input related to one or more characteristics of a pulse and provide first instructions to a plurality of control elements coupled to respective energy storage modules based on the first input; and
receive a second input related to one or more characteristics of a pulse and provide second instructions to the plurality of control elements coupled to respective energy storage modules based on the second input; wherein the first instructions comprise instructions to bypass a first subset of the energy storage modules of the first plurality of energy storage modules and/or the second plurality of energy storage modules and wherein the second instructions comprise instructions to bypass a second subset of the energy storage modules of the first plurality of energy storage modules and/or the second plurality of energy storage modules.

12. The system of claim 11, wherein the system operates in an energy balancing mode, wherein subsequent subsets comprise energy storage modules not included in prior subsets.

13. The system of claim 11, wherein the second subset is larger than the first subset and wherein a pulsed electric field generated by the second input has higher amplitude than a pulsed electric field generated by the first input.

14. The system of claim 11, wherein the first subset or the second subset comprises only energy storage modules from the first plurality of energy storage modules and not from the second plurality of energy storage modules.

15. The system of claim 11, wherein the first subset or the second subset comprises only energy storage modules from the second plurality of energy storage modules and not from the first plurality of energy storage modules.

16. The system of claim 11, comprising:
a cuvette coupling the positive chain and the negative chain to the load, wherein the cuvette comprises:
electrodes disposed on opposite sides of a dielectric containment element, the electrodes comprising a tapered upper portion.

* * * * *